United States Patent [19]

Hoek et al.

[11] Patent Number: 4,590,176
[45] Date of Patent: May 20, 1986

[54] CATALYST FOR DIMETHYL ETHER SYNTHESIS AND A PROCESS FOR ITS PREPARATION

[75] Inventors: Arend Hoek, Amsterdam, Netherlands; Martin F. M. Post, Houston, Tex.; Johannes K. Minderhoud, Amsterdam, Netherlands

[73] Assignee: Shell Oil Company, Houston, Tex.

[21] Appl. No.: 720,224

[22] Filed: Apr. 5, 1985

[30] Foreign Application Priority Data

Jun. 5, 1984 [NL] Netherlands ................... 8401790

[51] Int. Cl.$^4$ .................. B01J 21/04; B01J 23/06; B01J 23/26; B01J 23/72
[52] U.S. Cl. .................................... 502/307; 502/342; 518/713
[58] Field of Search ................ 502/307, 342; 518/713

[56] References Cited

U.S. PATENT DOCUMENTS

| | | | |
|---|---|---|---|
| 4,098,809 | 7/1978 | Pagani | 518/713 |
| 4,177,167 | 12/1979 | Manara et al. | 252/455 |
| 4,341,069 | 7/1982 | Bell et al. | 60/39.02 |
| 4,423,155 | 12/1983 | Bell et al. | 502/38 |

FOREIGN PATENT DOCUMENTS 2097382 11/1982 United Kingdom .

Primary Examiner—W. J. Shine

[57] ABSTRACT

A catalyst for the production of dimethyl ether from syngas, which comprises mixing a dehydration catalyst with a methanol synthesis catalyst comprising copper, zinc, chromium and/or aluminum which has been prepared by low-temperature co-precipitation from an aqueous solution containing specified amounts of the metals concerned.

14 Claims, No Drawings

CATALYST FOR DIMETHYL ETHER SYNTHESIS AND A PROCESS FOR ITS PREPARATION

FIELD OF THE INVENTION

The invention relates to a catalyst and the process for preparing it, which catalyst is suitable for the conversion of a mixture of carbon monoxide and hydrogen into dimethyl ether.

BACKGROUND OF THE INVENTION

The preparation of dimethyl ether from a $H_2/CO$ mixture can be carried out either in two steps or in a single step. In the two-step preparation the $H_2/CO$ mixture is converted in the first step into methanol by contacting it with a methanol synthesis catalyst, and subsequently the methanol formed is converted in a second step into dimethyl ether by contacting it with a dehydration catalyst. The development of the reaction in the two-step process may be rendered as follows.

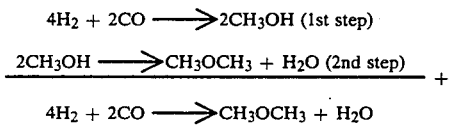

Among the methanol synthesis catalysts those containing copper, zinc and/or aluminum figure largely. They can be prepared by drying and calcining a co-precipitate obtained by adding a basic reacting substance to an aqueous solution in which the metals concerned are present in such quantities that the following requirements are met:
(a) the Cu/Zn atomic ratio is lower than 10,
(b) the (Cr+Al)/Cu+Zn) atomic ratio is lower than 2, and
(c) the Cu/(Cu+Zn+Cr+Al) atomic ratio is higher than 0.1.

It has been found that in the above-mentioned catalysts the activity for the conversion of a $H_2/CO$ mixture into methanol is to a great extent dependent on the temperature at which the co-precipitation is carried out. According as the co-precipitation is carried out at a higher temperature, the activity of the catalysts obtained will be higher. It has further been found that for the preparation of catalysts having an acceptable activity for the conversion of a $H_2/CO$ mixture into methanol on a technical scale the temperatures applied in the co-precipitation should be higher than 80° C. Contrary to their activity, the stability of these catalysts for the conversion of a $H_2/CO$ mixture into methanol is found to be virtually independent of the temperature applied in the co-precipitation. Both catalysts for which the co-precipitation was carried out at a high temperature and catalysts for which the co-precipitation was carried out at a low temperature have a high stability for the preparation of methanol from a $H_2/CO$ mixture.

The single-step preparation of dimethyl ether from a $H_2/CO$ mixture can be carried out by contacting the $H_2/CO$ mixture with a mixture of a methanol synthesis catalyst and a dehydration catalyst. The development of the reaction in the single-step process may be rendered as follows:

For the preparation of dimethyl ether from a $H_2/CO$ mixture there is a marked preference for the single-step process rather than the two-step process, the reasons being the following. Firstly, the maximum achievable equilibrium conversion is considerably higher for the single-step process than for the two-step process. Further, as shown by the reaction equations given hereinbefore, the two-step process requires the use of a hydrogen-rich $H_2/CO$ mixture, whereas for the single-step process a low-hydrogen $H_2/CO$ mixture suffices as feed. This is of particular interest, since nature provides large amounts of material with a relatively low H/C ratio, such as coal, which when used as starting material for the preparation of $H_2/CO$ mixtures, yield low-hydrogen mixtures. Finally, for application on a technical scale a single-step process is more attractive, obviously, than a two-step process.

An investigation into the single-step preparation of dimethyl ether over a mixture of a methanol synthesis catalyst and a dehydration catalyst, in which the methanol synthesis catalyst used was a catalyst for which the co-precipitation had been carried out at a temperature above 80° C. has revealed that this catalyst mixture had a high activity, but a low stability. Further investigation showed that the stability of these catalyst mixtures is to a great extent dependent on the temperature at which the co-precipitation of the methanol synthesis catalyst present therein has been carried out. According as this co-precipitation has been carried out at a lower temperature, the catalyst mixtures have a higher stability. It was found that in order to compose catalyst mixtures having an acceptable stability for the conversion on a technical scale of a $H_2/CO$ mixture into dimethyl ether, in the catalyst mixture use should be made of a methanol synthesis catalyst for which the co-precipitation has been carried out at a temperature below about 70° C. Unlike their stability, the activity of these catalyst mixtures for the conversion of $H_2/CO$ mixture into dimethyl ether is found to be virtually independent of the temperature applied in the co-precipitation. Both catalyst mixtures containing a methanol synthesis catalyst for which the co-precipitation has been carried out at a low temperature and those containing a methanol synthesis catalyst for which the co-precipitation has been carried out at a high temperature have a high activity for the preparation of dimethyl ether from a $H_2/CO$ mixture.

The above-described investigation has led to the conclusion that there is a radical difference in the extent to which the temperature at which the co-precipitation of the methanol synthesis catalyst is carried out influences the performance of this catalyst, depending on whether this catalyst is used per se for the preparation of methanol, or whether it is used in the form of a catalyst mixture together with a dehydration catalyst for the preparation of dimethyl ether. It is now possible to compose catalyst mixtures for the single-step conversion of a $H_2/CO$ mixture into dimethyl ether, which catalyst mixtures have both a high activity and a high stability.

SUMMARY OF THE INVENTION

The present patent application relates to a catalyst mixture for dimethyl ether synthesis and to a process for the preparation of said catalyst mixture, in which process a dehydration catalyst is mixed with a composition which comprises copper, zinc, chromium and/or aluminum and which has been obtained starting from an aqueous solution in which salts of the metal involved are present in such quantities that in the solution the following requirements are met:

(a) the Cu/Zn atomic ratio is lower than 10,
(b) the (Cr+Al)/(Cu+Zn) atomic ratio is lower than 2, and
(c) the Cu/(Cu+Zn+Cr+Al) atomic ratio is higher than 0.1, by adding to this solution at a temperature below about 70° C. a basic reacting or precipitating substance, followed by drying and calcining of the co-precipitate obtained.

The catalyst mixture is particularly useful for the single-step conversion of hydrogen and carbon monoxide to dimethyl ether. The instant catalyst mixtures provide higher stabilities than prior art catalysts. Thus, the instant catalyst mixtures, when used in the single-step conversion of hydrogen and carbon monoxide to dimethyl ether, provide for an important dimethyl ether synthesis process which can be run for longer periods of time prior to catalyst replacement.

DESCRIPTION OF THE PREFERRED EMBODIMENTS

In the process according to the invention use is made of a co-precipitate which has been obtained by adding a basic reacting substance to an aqueous solution containing salts of the metals involved. The basic reacting substance is preferably used in the form of an aqueous solution. Suitable basic reacting substances which can be used in the preparation of the metal-containing co-precipitate are, for example, ammonia, sodium carbonate, ammonium carbonate and alkali metal hydroxides. Thus, the basic reacting substances which may be used include ammonia, carbonates, bicarbonates and hydroxides of the alkali metals. The co-precipitation is preferably carried out in a mixing unit which provides a continuous supply of an aqueous solution comprising the metal salts involved and an aqueous solution of the basic reacting substance in stoichiometric quantity, calculated on the metals involved, and a continuous discharge of the co-precipitate formed. Advisably, before the co-precipitate is dried, it should be allowed to age for some time in the mother liquor and be subsequently thoroughly washed with water. The co-precipitation should be carried out at a temperature below about 70° C. and above about 5° C. Thus, the co-precipitation should be carried out at a temperature below about 70° C., preferably below about 60° C. and above about 10° C. and in particular below about 55° C. and above about 15° C.

In the process according to the invention the co-precipitation should be carried out starting from an aqueous solution in which the salts of the metals involved are present in such a ratio that in the solution the following requirements are met:

(a) the Cu/Zn atomic ratio is lower than 10,
(b) the (Cr+Al)/(Cu+Zn) atomic ratio is lower than 2, and
(c) the Cu/(Cu+Zn+Cr+Al) atomic ratio is higher than 0.1.

The preferred starting material is a solution in which the Cu/Zn atomic ratio is lower than 5 and in which the (Cr+Al)/(Cu+Zn) atomic ratio is lower than 1.

The co-precipitates that are used according to the invention should comprise copper and zinc and, in addition, chromium and/or aluminium. Preference is given to Cu/Zn/Cr and Cu/Zn/Cr/Al co-precipitates.

In the preparation of the catalyst mixture according to the invention the co-precipitate is mixed with a dehydration catalyst after being dried and calcined. Suitable dehydration catalysts are gamma-alumina, silica-alumina and crystalline aluminum silicates. Preference is given to the use of gamma-alumina as dehydration catalyst. In the catalyst mixture the mixing ratio between the composition obtained by co-precipitation and the dehydration catalyst may vary within wide ranges. The weight ratio between the two components of the catalyst mixture is preferably chosen between about 1:3 and about 3:1, and in particular between about 1:2 and about 2:1.

The catalyst mixtures prepared according to the process of the invention are excellently suitable for use in the conversion of a $H_2/CO$ mixture into dimethyl ether. The present patent application therefore also relates to a process for the conversion of a $H_2/CO$ mixture into dimethyl ether over a catalyst that has been prepared according to the invention.

Preparatory to being suitable for this use, the catalyst mixtures should be reduced. This reduction is preferably carried out at a temperature of about 150° C. to about 350° C. Reduction may be carried out in situ, i.e. by contact with the reducing $H_2/CO$ gas or in a separate step prior to contact with the $H_2/CO$ gas. Pre-reduction is preferable.

Preferably the $H_2/CO$ mixture used has a $H_2/CO$ molar ratio of about 0.5 to about 1.5. Examples of suitable $H_2/CO$ mixtures which are eligible for use as feed in the process are $H_2/CO$ mixtures obtained during the gasification of heavy carbonaceous materials, such as coal and $H_2/CO$ mixtures obtained in the steam reforming or partial oxidation of light hydrocarbons such as natural gas. The feed used by preference is a $CO_2$-containing $H_2/CO$ mixture, in particular a $H_2/CO/CO_2$ mixture comprising 0.5–25%v $CO_2$, calculated on $H_2/CO/CO_2$ mixture.

The conversion of $H_2/CO$ mixtures into dimethyl ether by using a catalyst mixture prepared according to the invention is preferably carried out at a temperature of about 175° to about 350° C. and in particular of about 200° to about 300° C., a pressure of about 5 to about 150 bar and in particular of about 20 to about 100 bar and a space velocity of about 100 to about 10000 Nl synthesis gas per 1 catalyst mixture per hour, and in particular of about 200 to about 5000 $Nl.l^{-1}.h^{-1}$.

The conversion of a $H_2/CO$ mixture into dimethyl ether by using a catalyst mixture prepared according to the invention can very suitably be carried out as an individual process. Optionally, unconverted synthesis gas can be recycled. The process can also be applied as the first step of a two-step process in which dimethyl ether, which has been formed in the first step, is catalytically converted in the second step into lower olefins and/or aromatic hydrocarbons. Very suitable catalysts for use in the second step of this process are crystalline metal silicates which are characterized in that, after one hour's calcination in air at about 500° C., they have the following properties:

(a) an X-ray powder diffraction pattern in which the strongest lines are the four lines mentioned in Table A

TABLE A

| d(Å) |
|---|
| 11.1 ± 0.2 |
| 10.0 ± 0.2 |

TABLE A-continued

| d(Å) |
|---|
| 3.84 ± 0.07 |
| 3.72 ± 0.06, and |

(b) in the formula which represents the composition of the silicate, expressed moles of the oxides, and which, in addition to $SiO_2$, includes one or more oxides of a trivalent metal M chosen from the group formed by iron, aluminium, gallium and boron, the $SiO_2/M_2O_3$ molar ratio is higher than 25.

The invention will be further described below by the following example which is provided for illustration, and is not to be construed as limiting the invention.

EXAMPLE

Five Cu/Zn/Cr co-precipitates (Co-precipitates 1-5) were prepared starting from two solutions (Solutions 1 and 2) which had been obtained by solving together in water copper nitrate, zinc nitrate and chromium nitrate. Solutions 1 and 2 were divided into two and three portions, respectively, and each one of these portions, together with a stoichiometric quantity of an aqueous ammonium carbonate solution, was pumped with stirring through a mixing unit which was kept at a constant temperature. The feed rate ratios were chosen such that the pH, measured at the discharge end of the mixing unit had a value between 6 and 7. The co-precipitates obtained were filtered off and washed with water until the wash water was free from nitrate ions. Co-precipitates 1-5 thus obtained were dried at 120° C., ground, and calcined for three hours at 300° C. to obtain Catalysts 1-5, respectively. The atomic ratios of the metals in Solutions 1 and 2 from which Co-precipitates 1-5 were prepared, and the temperatures at which the co-precipitations were carried out are given in Table B.

Five catalyst mixtures (I-V) were prepared by mixing gamma-alumina with equal quantities by weight of Catalysts 1-5, respectively.

Catalysts 3 and 5, and Catalyst Mixtures I-V were reduced in hydrogen at 220° C. and subsequently subjected to seven experiments (Experiments 1-7) to test them in the conversion of $H_2/CO/CO_2$ mixtures. All the experiments were carried out at a pressure of 60 bar. In Experiments 1 and 2, for the preparation of methanol, the starting material was a $H_2/CO/CO_2$ mixture having a molar ratio of 80/19/1. Experiments 1 and 2 were carried out at a temperature of 250° C. and a space velocity of 7000 $Nl.l^{-1}.h^{-1}$. In Experiments 3-7, for the preparation of dimethyl ether, the starting material was a $H_2/CO/CO_2$ mixture having a molar ratio of 49/49/2. Experiments 3-7 were carried out at a temperature of 270° C. and a space velocity of 500 $Nl.l^{-1}.h^{-1}$. The results of Experiments 1-7 are listed in Table C.

The following may be remarked on the data given in Tables B and C. Of the catalyst mixtures mentioned in Table C only Catalyst Mixtures II, IV and V have been prepared according to the invention. They were obtained starting from co-precipitates which had been prepared at a temperature below 70° C. Catalyst Mixtures I and III fall outside the scope of the invention. They have been included in the patent application for comparison. Both catalyst mixtures were obtained starting from co-precipitates which had been obtained at a temperature above 70° C. Of the experiments mentioned in Table C only Experiments 4, 5 and 7 were carried out by using a catalyst mixture which had been prepared according to the invention. The other experiments have been included in the patent application for comparison.

Comparison of the results of Experiments 1 and 2 reveals the influence of the temperature of precipitation on the performance of the catalyst during the preparation of methanol. In Experiment 1 the catalyst (precipitation temperature 19° C.) shows a low activity. In Experiment 2 the catalyst (precipitation temperature 90° C.) shows a high activity. In both cases the stability of the catalyst is high.

Comparison of Experiments 3-5 in relation to one another and of Experiments 6 and 7 in relation to one another shows the influence of the precipitation temperature on the performance of the catalyst mixture during the preparation of dimethyl ether. In Experiments 3 and 6 the catalyst mixtures (precipitation temperatures 90° and 86° C., respectively) show a low stability. In Experiments 4, 5 and 7 the catalyst mixtures (precipitation temperatures 19°, 50° and 40° C., respectively) show a high stability. In all these cases the catalyst mixtures have a high activity.

TABLE B

| Catalyst No. | Atomic ratio of the metals in the solution | | | Temperature used during the co-precipitation, °C. |
|---|---|---|---|---|
| | Cu | Zn | Cr | |
| 1 | 50 | 30 | 20 | 86 |
| 2 | 50 | 30 | 20 | 48 |
| 3 | 25 | 48 | 27 | 90 |
| 4 | 25 | 48 | 27 | 50 |
| 5 | 25 | 48 | 27 | 19 |

TABLE C

| Experiment No. | 1 | 2 | 3 | 4 | 5 | 6 | 7 |
|---|---|---|---|---|---|---|---|
| Catalyst or catalyst mixture used in the experiment | 5 | 3 | III | V | IV | I | II |
| Catalyst number of catalyst present in catalyst mixture | — | — | 3 | 5 | 4 | 1 | 2 |
| Initial conversion of the feed, % vol | 28 | 46 | 87 | 87 | 87 | 87 | 86 |
| Loss of conversion, % vol per 100 hours | <1 | <1 | 7 | 1 | 2 | 8 | 3 |

We claim:

1. A process for the preparation of a catalyst mixture, which comprises mixing a dehydration catalyst with a composition comprising copper, zinc, chromium and/or aluminum, which composition has been obtained starting from an aqueous solution in which salts of the metals concerned are present in such quantities that in the solution the following requirements are met:

(a) the Cu/Zn atomic ratio is lower than 10, (b) the (Cr+Al)/(Cu+Zn) atomic ratio is lower than 2, and (c) the Cu/(Cu+Zn+Cr+Al) atomic ratio is higher than 0.1, and adding to this solution at a temperature below about 55° C. and above about 15° C. a basic reacting substance to effect co-precipitation, followed by drying and calcining of the co-precipitate obtained.

2. The process of claim 1, wherein the basic reacting substance is selected from the group consisting of ammonia, an alkali metal carbonate, an alkali metal bicarbonate, an alkali metal hydroxide and mixtures thereof.

3. The process of claim 1, wherein the co-precipitate has been obtained starting from an aqueous solution in which the Cu/Zn atomic ratio is lower than 5 and the (Cr+Al)/(Cu+Zn) atomic ratio is lower than 1.

4. The process of claim 1, wherein the dehydration catalyst used is a gamma-alumina.

5. The process of claim 1, wherein the weight ratio between the two components of the catalyst mixture is chosen between about 1:3 and about 3:1.

6. The process of claim 1, wherein the weight ratio between the dehydration catalyst and the composition comprising copper, zinc, chromium and/or aluminum is chosen between about 1:2 and about 2:1.

7. The process of claim 1, wherein the catalyst mixture is reduced at a temperature in the range between about 150° C. and about 350° C.

8. A catalyst mixture made by a process which comprises mixing a dehydration catalyst with a composition comprising copper, zinc, chromium and/or aluminum, which composition has been obtained starting from an aqueous solution in which salts of the metals concerned are present in such quantities that in the solution the following requirements are met:
 (a) the Cu/Zn atomic ratio is lower than 10,
 (b) the (Cr+Al)/(Cu+Zn) atomic ratio is lower than 2, and
 (c) the Cu/(Cu+Zn+Cr+Al) atomic ratio is higher than 0.1,
and adding to this solution at a temperature below about 55° C. and above about 15° C. a basic reacting substance to effect co-precipitation, followed by drying and calcining of the co-precipitate obtained.

9. The catalyst mixture of claim 8, wherein, in the process, the basic reacting substance is selected from the group consisting of ammonia, an alkali metal carbonate, an alkali metal bicarbonate, an alkali metal hydroxide and mixtures thereof.

10. The catalyst mixture of claim 8, wherein, in the process, the co-precipitate has been obtained starting from an aqueous solution in which the Cu/Zn atomic ratio is lower than 5 and the (Cr+Al)/(Cu+Zn) atomic ratio is lower than 1.

11. The catalyst mixture of claim 8, wherein, in the process, the dehydration catalyst used is gamma-alumina.

12. The catalyst mixture of claim 8, wherein, in the process, the weight ratio between the dehydration catalyst and the composition comprising copper, zinc, chromium and/or aluminum is chosen between about 1:3 and about 3:1.

13. The catalyst mixture of claim 8, wherein, in the process, the weight ratio between the dehydration catalyst and the composition comprising copper, zinc, chromium and/or aluminum is chosen between about 1:2 and about 2:1.

14. The catalyst mixture of claim 8, wherein, in the process, the catalyst mixture is reduced at a temperature in the range between about 150° C. and about 350° C.

* * * * *